US011033244B2

(12) United States Patent
Lim et al.

(10) Patent No.: US 11,033,244 B2
(45) Date of Patent: Jun. 15, 2021

(54) IN VIVO RADIATION AMOUNT MEASURING INSTRUMENT USING FILM DOSIMETER THAT UNDERGOES SHAPE CHANGE WITH EXPANSION

(71) Applicant: NATIONAL CANCER CENTER, Goyang-si (KR)

(72) Inventors: Young Kyung Lim, Paju-si (KR); Eun Hee Jeang, Paju-si (KR); Ui-Jung Hwang, Goyang-si (KR); Kwan Ho Cho, Seodaemun-gu (KR); Se Byeong Lee, Goyang-si (KR); Dongho Shin, Suwon-si (KR); Jeonghoon Park, Yeongdeungpo-gu (KR); Dae Yong Kim, Goyang-si (KR); Joo-Young Kim, Goyang-si (KR); Tae Hyun Kim, Gangnam-gu (KR); Sun Young Kim, Yeongdeungpo-gu (KR); Kwanghyun Jo, Gangnam-gu (KR); Ki Mun Kang, Jinju-si (KR); Hojin Jeong, Jinju-si (KR)

(73) Assignee: NATIONAL CANCER CENTER, Goyang-Si (KR)

( * ) Notice: Subject to any disclaimer, the term of this patent is extended or adjusted under 35 U.S.C. 154(b) by 847 days.

(21) Appl. No.: 15/567,697

(22) PCT Filed: Mar. 4, 2016

(86) PCT No.: PCT/KR2016/002204
§ 371 (c)(1),
(2) Date: Oct. 19, 2017

(87) PCT Pub. No.: WO2016/171388
PCT Pub. Date: Oct. 27, 2016

(65) Prior Publication Data
US 2018/0098742 A1    Apr. 12, 2018

(30) Foreign Application Priority Data

Apr. 20, 2015 (KR) .................. 10-2015-0055491

(51) Int. Cl.
*A61B 6/00* (2006.01)
*A61B 5/00* (2006.01)
(Continued)

(52) U.S. Cl.
CPC ............... *A61B 6/425* (2013.01); *A61B 5/68* (2013.01); *A61M 25/1002* (2013.01);
(Continued)

(58) Field of Classification Search
CPC . A61B 6/425; A61B 5/68; A61B 2017/00022; A61N 5/1071; A61N 5/1014;
(Continued)

(56) References Cited

U.S. PATENT DOCUMENTS 3,665,916 A * 5/1972 Kobayashi ............ A61M 25/04
600/436
6,484,050 B1 * 11/2002 Carroll .................. A61B 6/032
250/362

(Continued)

FOREIGN PATENT DOCUMENTS

JP    H09-61202 A    3/1997
KR    10-0921342 B1    10/2009
(Continued)

OTHER PUBLICATIONS

Wadhwani, "Parylene Coatings and Applications" PCI, Oct. 1, 2006 (Year: 2006).*

(Continued)

*Primary Examiner* — Serkan Akar
*Assistant Examiner* — Aminah Asghar
(74) *Attorney, Agent, or Firm* — McCarter & English, LLP

(57) ABSTRACT

The present invention relates to an in vivo radiation amount measuring instrument. An in vivo radiation amount measuring instrument according to the present invention comprises: a main body elongated along an in vivo inserting direction and capable of supplying a fluid; an expanding part having at least a portion thereof fixed or connected to the main body and capable of being expanded and contracted by means of the outflow/inflow of the fluid; and a radiation measuring part disposed on the expanding part and measuring the amount of surface radiation distribution on in vivo tissue which the expanding part contacts by expanding.

15 Claims, 13 Drawing Sheets

(51) Int. Cl.
| | | |
|---|---|---|
| *A61M 25/10* | (2013.01) | |
| *A61N 5/10* | (2006.01) | |
| *A61B 17/00* | (2006.01) | |

(52) U.S. Cl.
CPC .. *A61N 5/1071* (2013.01); *A61B 2017/00022* (2013.01); *A61M 2025/1086* (2013.01); *A61N 5/1014* (2013.01)

(58) Field of Classification Search
CPC ............ A61N 5/1048; A61M 25/1002; A61M 2025/1086; G01T 1/02; G01T 1/08
See application file for complete search history.

(56) References Cited

U.S. PATENT DOCUMENTS

| | | | |
|---|---|---|---|
| 2004/0230178 A1* | 11/2004 | Wu | A61M 25/0054 604/527 |
| 2005/0080313 A1 | 4/2005 | Stewart et al. | |
| 2006/0259061 A1* | 11/2006 | Kick | A61M 29/02 606/191 |
| 2010/0288934 A1* | 11/2010 | Keppel | A61N 5/1071 250/362 |
| 2012/0215053 A1 | 8/2012 | Gim | |
| 2012/0259197 A1* | 10/2012 | Isham | A61N 5/10 600/407 |
| 2013/0085315 A1 | 4/2013 | Isham et al. | |
| 2013/0109906 A1* | 5/2013 | Valoir | A61M 25/1002 600/3 |
| 2013/0317276 A1 | 11/2013 | D'Andrea | |
| 2018/0036555 A1* | 2/2018 | Suh | A61B 90/17 |
| 2018/0344989 A1* | 12/2018 | Laduca | A61M 25/0155 |

FOREIGN PATENT DOCUMENTS

| | | |
|---|---|---|
| WO | WO-1999/12609 A1 | 3/1999 |
| WO | 2003/003923 A2 | 1/2003 |

OTHER PUBLICATIONS

European Search Report for Application No. 16783322.7 dated Jan. 3, 2019, pp. 1-6.
International Search Report and Written Opinion for Application No. PCT/KR2016/002204, dated Jul. 25, 2016. 2 pages.

\* cited by examiner

IN VIVO RADIATION AMOUNT MEASURING INSTRUMENT USING FILM DOSIMETER THAT UNDERGOES SHAPE CHANGE WITH EXPANSION

RELATED APPLICATIONS

This application is a national stage filing under 35 U.S.C. § 371 of International Application No. PCT/KR2016/002204, filed Mar. 4, 2016, which claims priority to Korean Patent Application No. 10-2015-0055491, filed Apr. 20, 2015. The entire contents of each of the aforementioned applications are hereby incorporated by reference in their entirety.

BACKGROUND OF THE INVENTION

Field of the Invention

The present invention relates to an in vivo radiation dose measuring device.

Related Art

Generally, radiation therapy treats cancer by using high-energy X-ray, gamma ray, electron beam, proton beam, carbon ion beam, or the like, to damage tumor cells and induce apoptosis. Therefore, in order to maximize the damage to tumor cells, as much radiation as possible needs to be delivered to tumors.

However, radiation therapy affects not only tumors but also normal organs around the tumors. If a lot of radiation is irradiated to normal organs, side effects of radiation may occur.

Therefore, the dose of radiation delivered to normal organs should be accurately measured. However, since only the dose of radiation at one point was measured in the conventional art, it is not possible to predict the occurrence of side effects of radiation and it is difficult to find an exact relationship between the dose of radiation delivered and the side effect of radiation.

SUMMARY OF THE INVENTION

An aspect of the present invention is to provide a technique for measuring an accurate two-dimensional dose distribution of radiation delivered to an in vivo tissue by radiation therapy on a cancer patient.

In accordance with an aspect of the present invention, the present invention provides an in vivo radiation dose measuring device, including: a main body extending long in a direction of in vivo insertion and being capable of supplying a fluid; an expansion part having at least a portion fixed or connected to the main body and being expandable and shrinkable by inflow and outflow of the fluid; and a radiation measurement part disposed on the expansion part to measure a plane (2-dimensional) dose distribution of radiation in the in vivo tissue which the expansion part expands to touch.

The radiation measurement part may have a film type wrapping at least a portion of the expansion part, and the radiation measurement part may be unfolded upon the expansion of the expansion part, and returned to a form wrapping the expansion part prior to expansion upon the shrinkage of the expansion part.

The radiation measurement part may have one or more fold lines parallel with the direction of insertion, the fold lines being formed in a direction in which the radiation measurement part wraps the expansion part.

The in vivo radiation dose measuring device may further include an accommodation part accommodating the radiation measurement part, wherein the accommodation part is transformable in compliance with a shape change of the radiation measurement part.

The accommodation part and the expansion part may be in contact with each other, and at least one of the accommodation part and the expansion part may be formed of or treated with a material for reducing frictional force therebetween.

The accommodation part may have a pocket form and may be in close contact with the radiation measurement part.

The accommodation part may be formed of an elastic material.

The accommodation part may be formed of at least one of polyurethane, nylon, and polyester.

The expansion part may be formed of at least one of silicone, polyurethane, nylon, natural rubber, and synthetic rubber.

The expansion part may have a fixation element, and at least one of the radiation measurement part and the accommodation part may have a fixation counterpart correspondence to the fixation element.

The fixation element may protrude outward, and the fixation counterpart may include at least one of a hole and a coupling structure, which are formed in the radiation measurement part.

The in vivo radiation dose measuring device may further include a position indication part for allowing the understanding of an insertion position of the device from the outside upon the insertion of the device into the body.

The in vivo radiation dose measuring device may further include a position indication part for allowing the understanding of an insertion position of the device from the outside upon the insertion of the device into the body, wherein the position indication part is positioned on the fixation element.

The in vivo radiation dose measuring device may further include a shrinkage part formed outside the accommodation part, wherein the shrinkage part gives shrinking force to the radiation measurement part upon the shrinkage of the expansion part.

The shrinkage part may be formed of an elastic material.

The shrinkage part may be formed of at least one of polyurethane, nylon, polyester, silicone, natural rubber, and synthetic rubber.

The accommodation part may include: a first portion wrapping the expansion part; and a second portion connected with the first portion to wrap the radiation measurement part, wherein the accommodation part gives shrinking force to the expansion part.

The in vivo radiation dose measuring device may further include a shrinkage auxiliary part connected to a plurality of sites of the radiation measurement part, one end of the shrinkage auxiliary part protruding out of the body when the device is inserted into the body, wherein the shrinkage auxiliary part is capable of additionally shrinking the radiation measurement part by operating a portion protruding out of the body The shrinkage auxiliary part may shrink a portion of the radiation measurement part, which is close to the direction of in vivo insertion.

In accordance with an aspect of the present invention, the present invention provides an in vivo radiation dose measuring device, including: an extension part extending long in a direction of in vivo insertion and being capable of supplying a fluid to the outside; an expansion part having at least a portion fixed or connected to the extension part and being expandable and shrinkable by inflow and outflow of the fluid; and a radiation measurement part, which wraps at least a portion of the expansion part in an unfolded state upon the expansion of the expansion part and wraps the expansion part in an at least partly folded state upon of the shrinkage of the expansion part.

The radiation measurement part may measure the radiation dose in the body tissue corresponding to the expansion part in the plane dimension.

The radiation measurement part may be configured of a film, extend in the direction of insertion, and have one or more fold lines for determining the folded state.

According to the present invention, provided is an in vivo radiation dose measuring device for measuring an accurate two-dimensional dose distribution of radiation delivered to an in vivo tissue.

DESCRIPTION OF EXEMPLARY EMBODIMENTS

Hereinafter, the present invention will be described in detail with reference to accompanying drawings.

The accompanying drawings correspond to merely an example shown to illustrate technical scope of the present invention more detail, and the scope of the present invention is not limited to the accompanying drawings.

The following embodiments are described by exemplifying cases in which an in vivo radiation dose measuring device is inserted into the rectum, but the in vivo radiation dose measuring device according to the present invention, without the limitation to the rectum, may be used for female genitalia, oral cavity, nasal cavity, pharynx, esophagus, bronchus, and the like.

Figure 6:
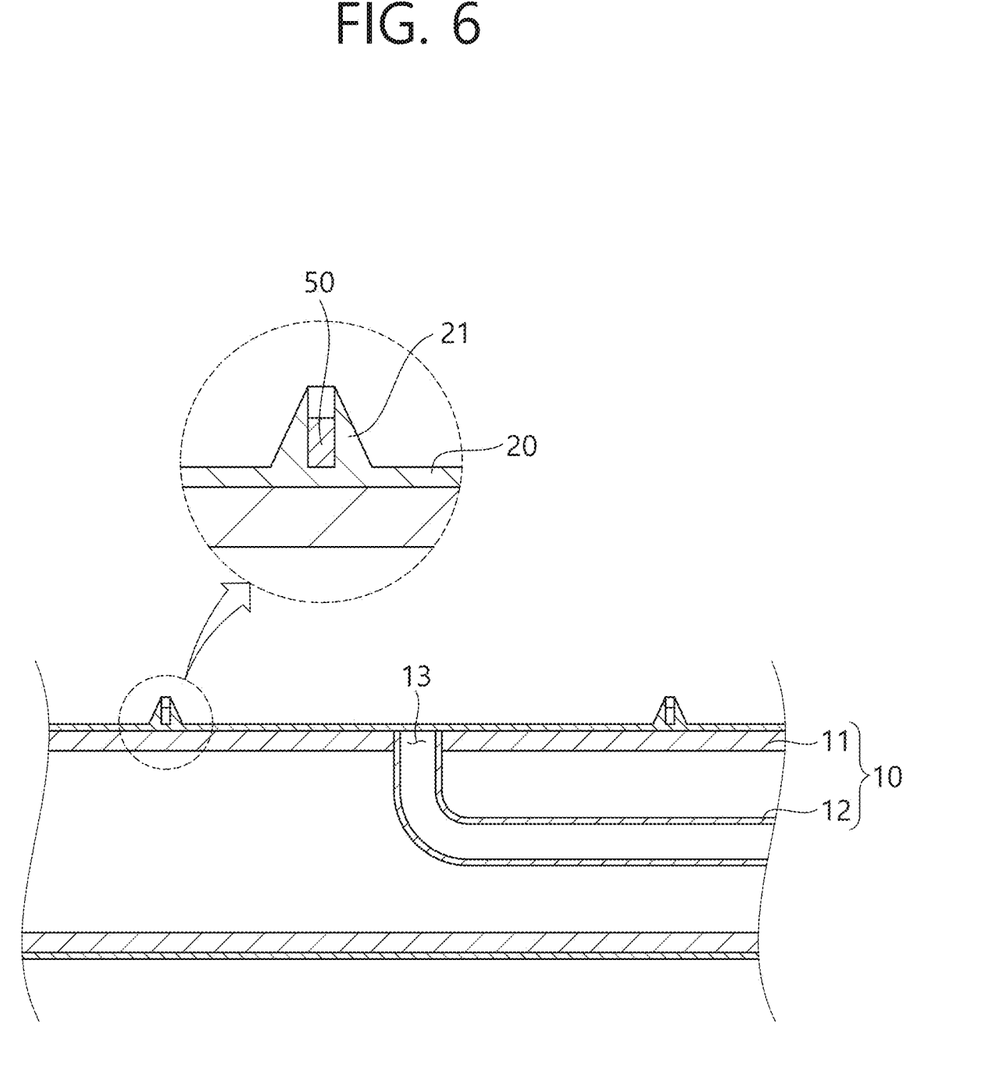
FIG. 6 is a cross-sectional view taken along line VI-VI' of FIG. 5.
Figure 7:
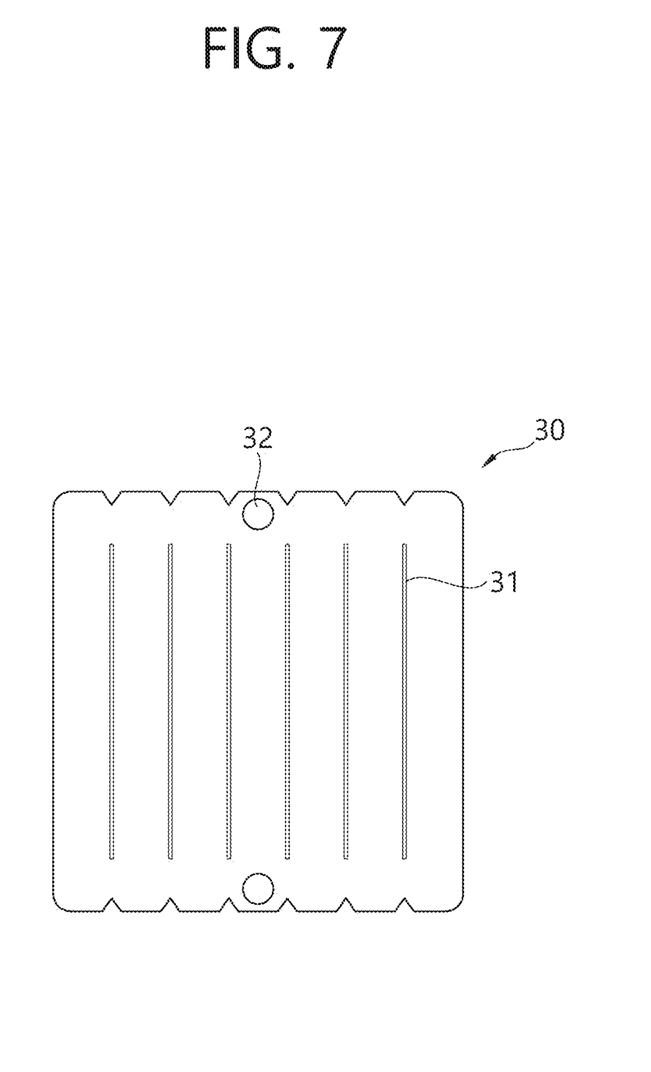
FIG. 7 is a plane view of a radiation measurement part of the in vivo radiation dose measuring device according to the first embodiment of the present invention.

An in vivo radiation dose measuring device according to a first embodiment of the present invention and a use thereof will be described with reference to FIGS. 1 and 7.

Figure 1:
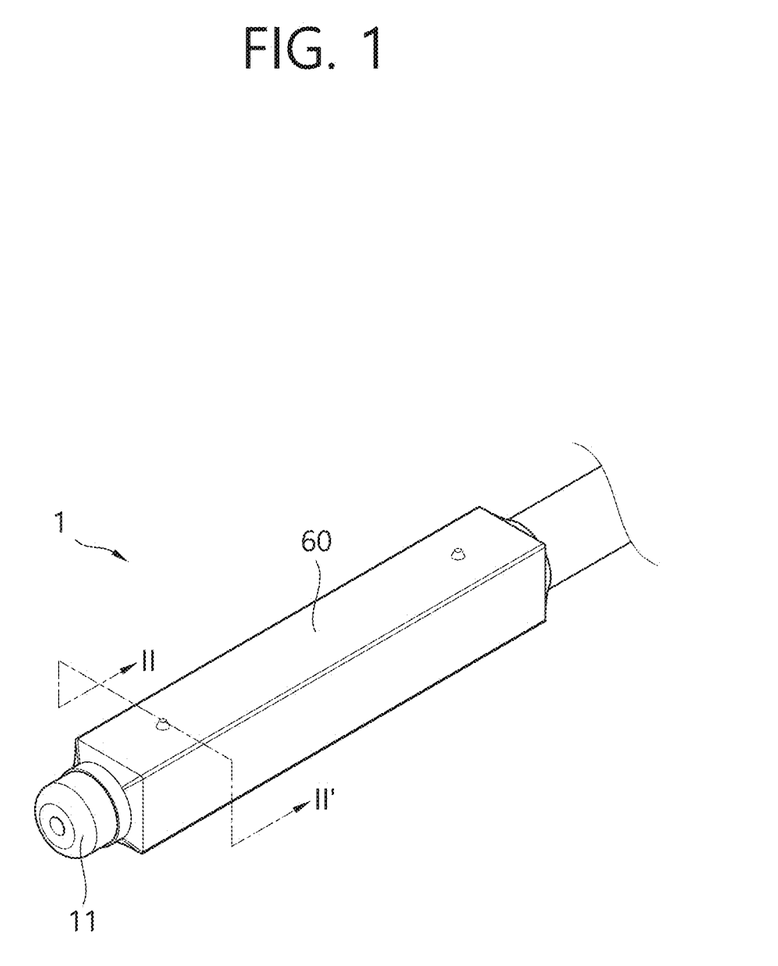
FIG. 1 is a perspective view showing a shrunken state of an in vivo radiation dose measuring device according to a first embodiment of the present invention.
Figure 2:
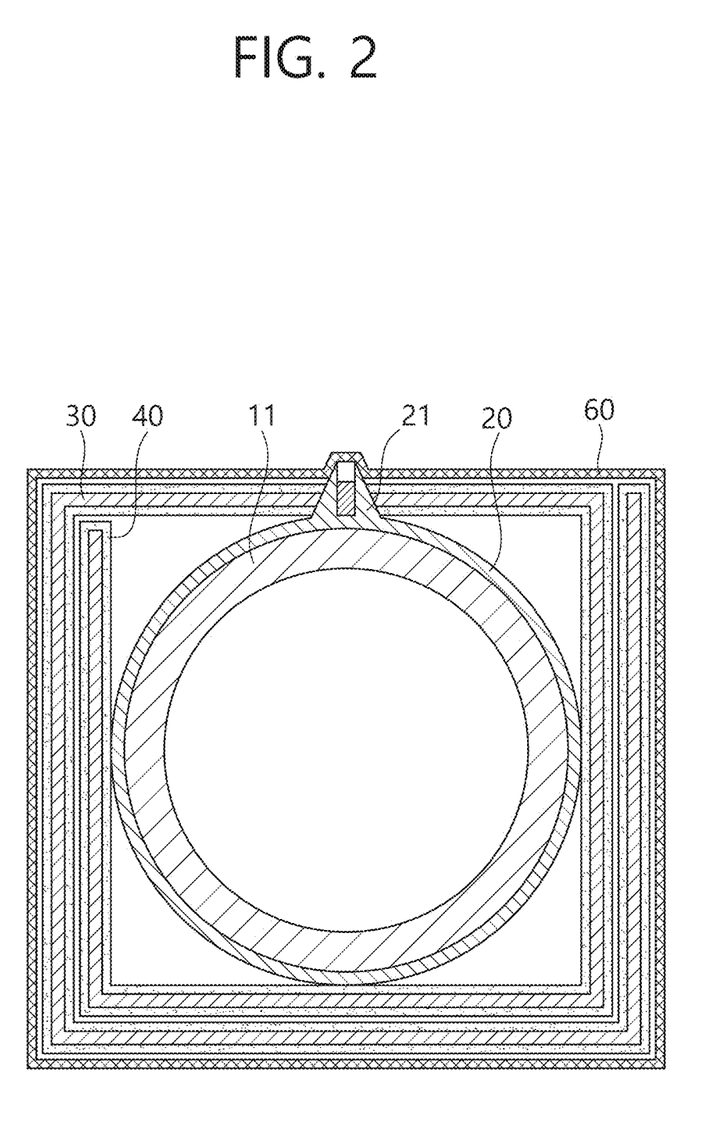
FIG. 2 is a cross-sectional view taken along line II-II' of FIG. 1.
Figure 3:
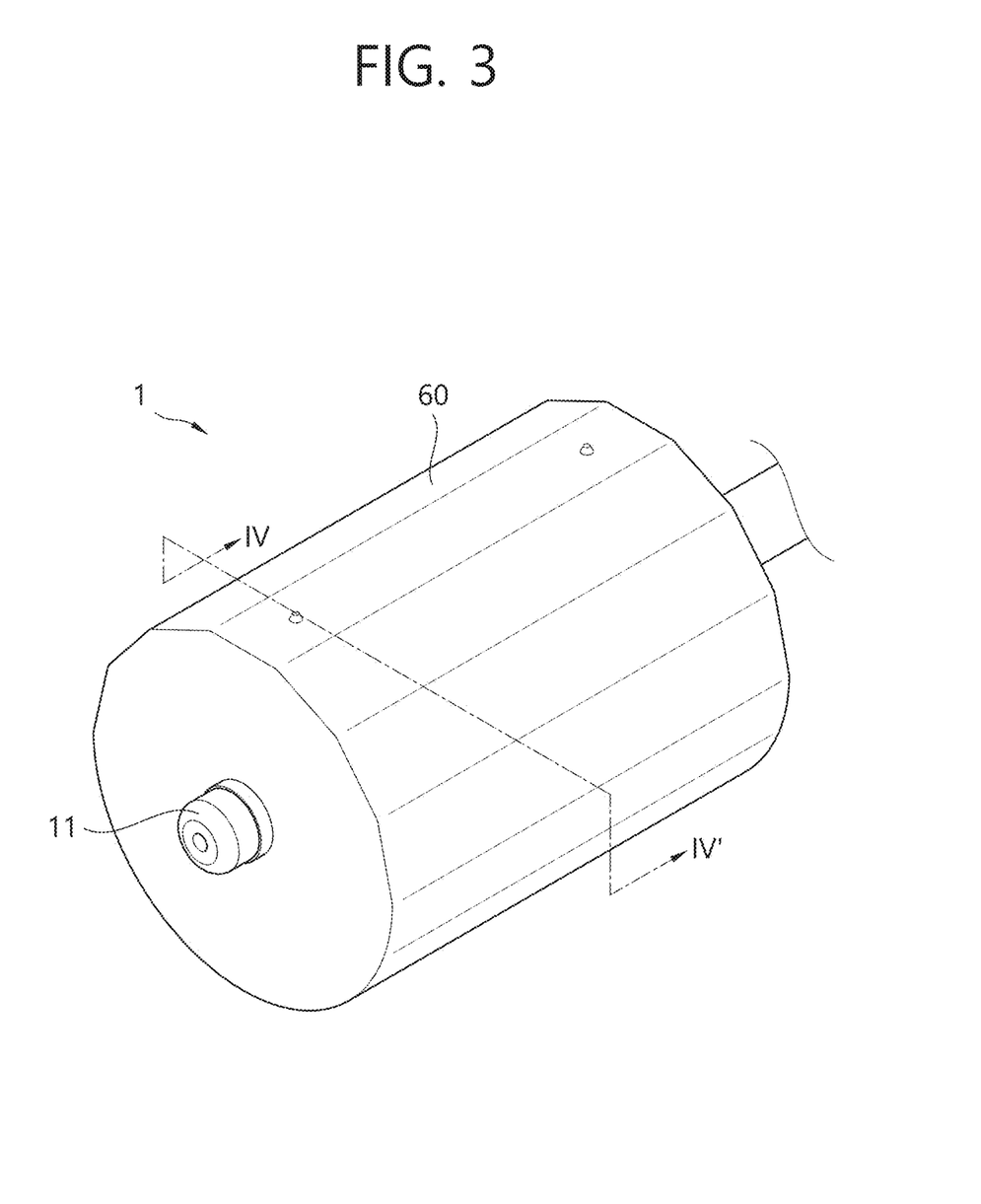
FIG. 3 is a perspective view showing an expanded state of the in vivo radiation dose measuring device according to the first embodiment of the present invention.
Figure 4:
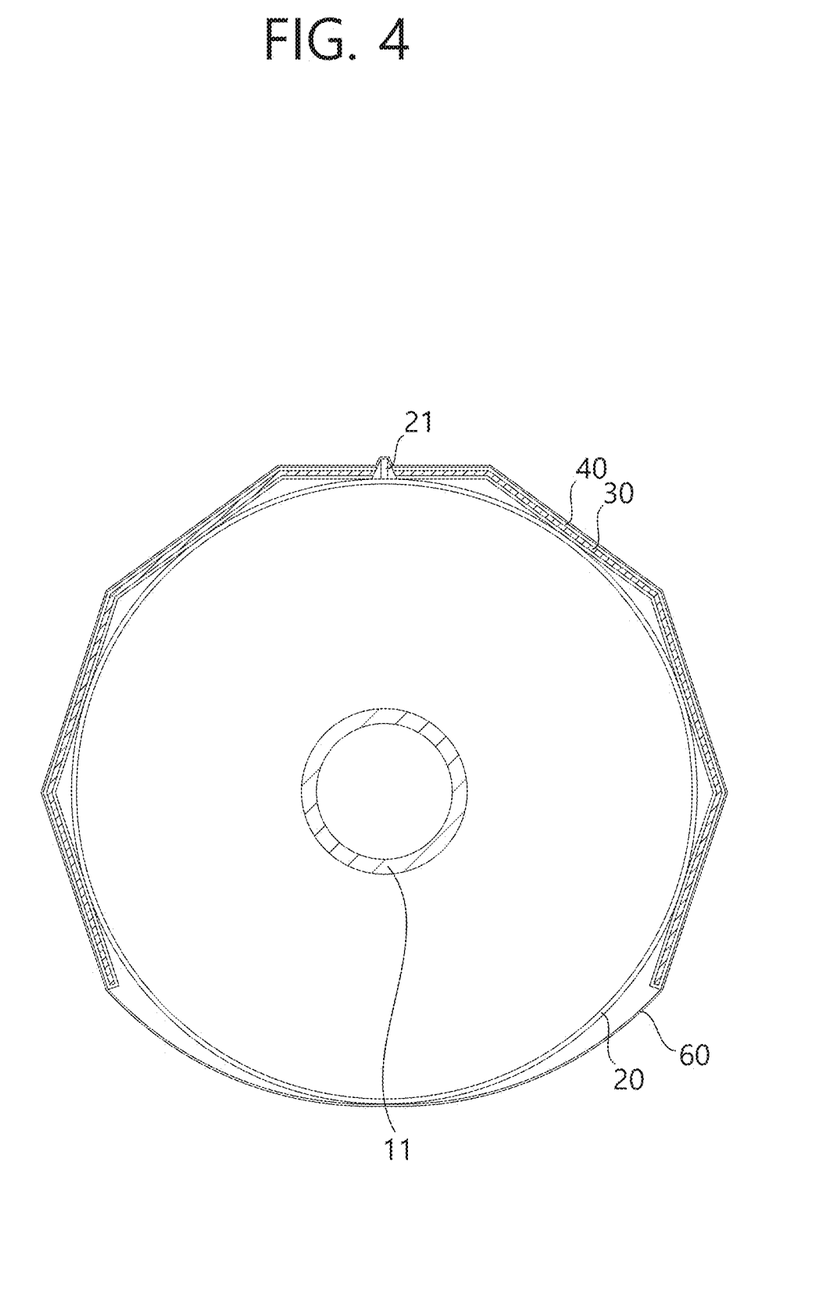
FIG. 4 is a cross-sectional view taken along line IV-IV' of FIG. 3.

FIG. 1 is a perspective view showing a shrunken state of an in vivo radiation dose measuring device according to a first embodiment of the present invention; FIG. 2 is a cross-sectional view taken along line II-II' of FIG. 1; FIG. 3 is a perspective view showing an expanded state of the in vivo radiation dose measuring device according to the first embodiment of the present invention; and FIG. 4 is a cross-sectional view taken along line IV-IV' of FIG. 3.

An in vivo radiation dose measuring device 1 according to a first embodiment of the present invention is inserted into the body through the anus in a shrunken state as shown in FIG. 1. Thereafter, the in vivo radiation dose measuring device expands as shown in FIG. 3. The in vivo radiation dose measuring device 1 performs radiation treatment on the prostate or the like in an expanded state, and measures an accurate two-dimensional does distribution of radiation delivered to the in vivo tissue.

The in vivo radiation dose measuring device 1 includes a main body 10, an expansion part 20, a radiation measurement part 30, an accommodation part 40, a position indication part 50, and a shrinkage part 60.

The expansion part 20 has a balloon type, and expands by receiving a fluid, such as air or water, from the main body 10, and again shrinks when the fluid flows out through the main body 10.

In the first embodiment, the radiation measurement part 30 has a film type, and is accommodated in a pocket type accommodation part 40. As the radiation measurement part 30, a dosimeter using radiation sensitization, including a radiation-sensitive film or the like, or a dosimeter using radiation ionization, including a diode array plate or the like, may be used.

The radiation indication part 50 is accommodated in the expansion part 20, and formed of a material allowing the understanding of the position by an X-ray image. In another embodiment, the position indication part 50 may be attached to another element or may be prepared as one body with another element.

A portion of the radiation measurement part 30 is fixed to the expansion part 20, and the description thereof will be described later.

The shrinkage part 60 wraps the accommodation part, and gives shrinking force to the accommodation unit 40. Although not shown, the in vivo radiation dose measurement device 1, when actually used, may be used by covering an outside of the shrinkage part 60 with a separate waterproof cover as needed.

As shown in FIG. 2, in a shrunken state, the radiation measurement part 30 wraps the entirety of the expansion part 20 in a polygonal shape, and a partial region of the expansion part 20 is wrapped by a plurality of layers. In a shrunken state, the radiation measurement part 30 maintains a form in which the radiation measurement 30 is in close contact with the expansion part 20 due to shrinking force.

As shown in FIG. 4, in an expanded state, the radiation measurement part 30 wraps only a portion of the expansion part 20 in a polygonal shape, and wraps the entirety of the expansion part in a single layer type. In addition, in an expanded state, the radiation measurement part 30 maintains a form in which the radiation measurement part 30 is in close contact with the expansion part 20 due to the shrinking force of the shrinkage part 60.

Hereinafter, the in vivo radiation dose measuring device 1 according to the first embodiment will be described in more detail with reference to FIGS. 5 to 7.

Figure 5:
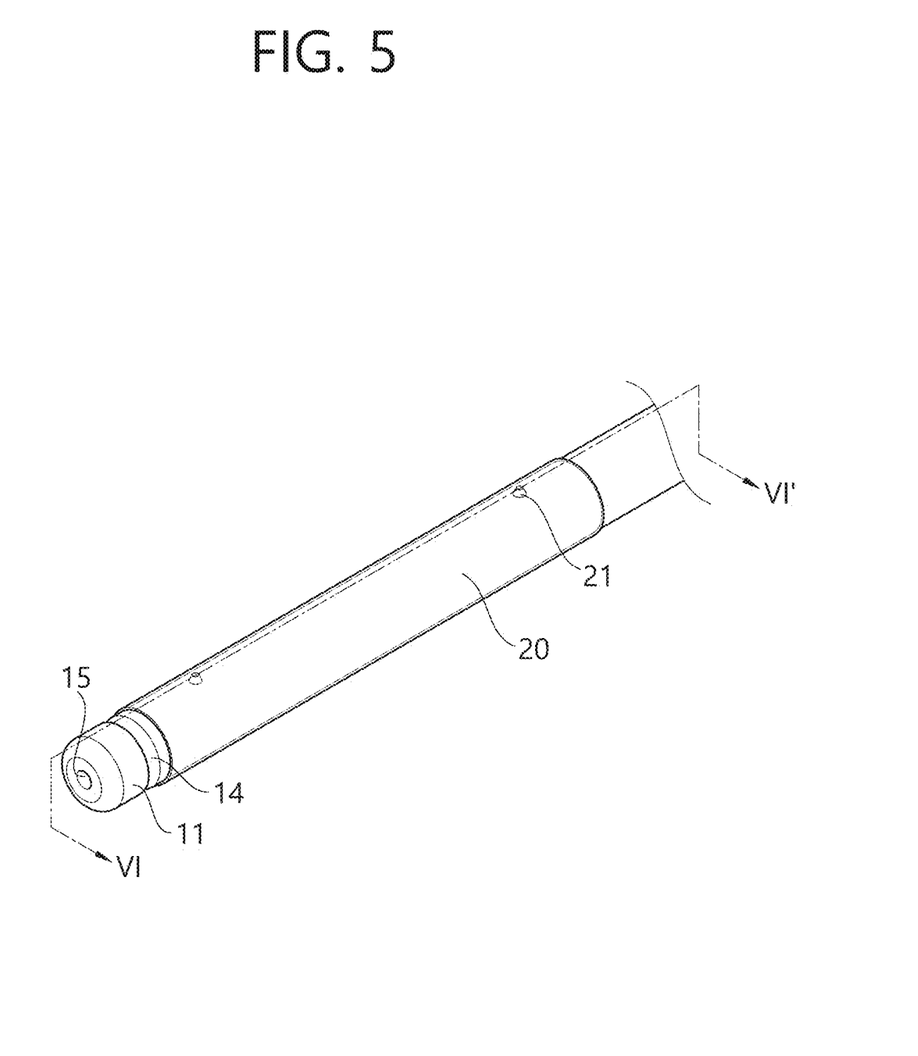
FIG. 5 is a perspective view of an expansion part of the in vivo radiation dose measuring device according to the first embodiment of the present invention.

FIG. 5 is a perspective view of an expansion part of the in vivo radiation dose measuring device according to the first embodiment of the present invention; FIG. 6 is a cross-sectional view taken along line VI-VI' of FIG. 5; and FIG. 7 is a plane view of a radiation measurement part of the in vivo radiation dose measuring device according to the first embodiment of the present invention.

The main body 10 includes a long tube-shaped main body tube 11 and a fluid supply tube 12. A fluid supply hole 13 connected to the expansion part 20 is formed in a middle region of the main body tube 11, and a mount groove 14 is formed into an end region of the main body tube 11. A gas outflow hole 15 for exhausting gas in the body is formed in an end portion of the main body tube 11 when the in vivo radiation dose measuring device is applied into the rectum. The gas outflow hole 15 becomes a passage for respiration of a patient when the in vivo radiation dose measuring device is applied into the oral cavity, nasal cavity, pharynx, bronchus, and the like.

The fluid supply tube 12 supplies a fluid from an air or water supply source (not shown) to the expansion part 20 through the fluid supply hole 13. Although not shown, there may be an opening/closing valve capable of controlling the supply and collection of the fluid through the fluid supply tube 12.

The expansion part 20 is in close contact with the main body tube 11 at the time of shrinkage, and has a pair of fixation elements 21 protruding outward. In the expansion part 20 at the time of expansion, both ends are in close contact with the main body tube 11 to keep the airtightness and the middle region is inflated by the fluid. There is an accommodation space inside the fixation part 21, and the position indication part 50 is positioned in the accommodation space.

The expansion part 20 may be formed of a silicone material, which may be silicone, polyurethane, nylon, natural rubber, or synthetic rubber alone or a composite thereof. The expansion part 20 expands and shrinks according to the supply and collection of the fluid.

The position indication part 50 may be formed of any material that can be detected by an X-ray image, for example, a metal piece single material or a mixture of metal particles and a polymer. The position indication part 50 may be provided in a cylindrical shape in one embodiment, but may be provided in another shape, such as a spherical shape or a ring shape in another embodiment.

In the first embodiment, the radiation measurement part 30 may be a dosimeter type radiation film using radiation sensitization, and may be configured of multiple layers including a protective layer—a radiation-sensitive layer—a protection layer. The radiation measurement part 30 is generally rectangular in shape. The radiation measurement part 30 has fold lines 31 formed at predetermined intervals and fixation counterparts 32 corresponding to the fixation elements 21 of the expanding part 20.

The fold lines 31 are prepared through incisions in a length direction of the main body tube 11, and the fixation counterparts 32 are prepared in a hole type. A plurality of the fold lines 31 are formed in a direction in which the radiation measurement part 30 wraps the expansion part 20.

Although not shown, the radiation measurement part 30 may further comprise a distance maintenance element, which connects both sides, which are divided by the fold lines 31, to prevent both sides from excessively being apart. The distance maintenance element may employ an adhesive tape, but is not limited thereto.

The accommodation part 40 is formed in a pocket shape corresponding to the radiation measurement part 30, and a material for the accommodation part 40 may be a material having excellent shrinking force and restoring force. A specific example of the material may be polyurethane, nylon, and polyester alone or in a mixture thereof. The accommodation part 40 prevents the radiation measurement part 30 from being damaged by a direct contact with another component, especially, the expansion part 20, or from being affected by expanded and shrunken states through a contact with another component.

At least one of the accommodation part 40 and the expansion part 20 may be formed of a material for reducing frictional force therebetween or may be surface-treated to surface treatment for friction prevention, and the surface treatment for friction prevention may be a coating treatment with an anti-friction agent, a protrusion treatment on a surface, surface modification, or the like.

The shrinkage part 60 also has a pocket type, and one end portion of the shrinkage part 60 is mounted in the mount groove 14 of the main body. The shrinkage part 60 may also be formed of a material having excellent shrinking force and restoring force, and may be formed of polyurethane, silicone, natural rubber, synthetic rubber, polyurethane/nylon, or polyurethane/polyester.

Hereinafter, a use method and effects of the in vivo radiation dose measuring device 1 according to the first embodiment of the present invention will be described.

The in vivo radiation dose measuring device 1 in a shrunken state is inserted into the body through the anus of a prostatic cancer patient. After the insertion into the body, the in vivo radiation dose measuring device 1 is converted into an expanded state through the supply of a fluid. The position of the position indication part 50 is understood by using an X-ray image, and then the position of the entire in vivo radiation dose measuring device 1 is controlled.

Figure 8:
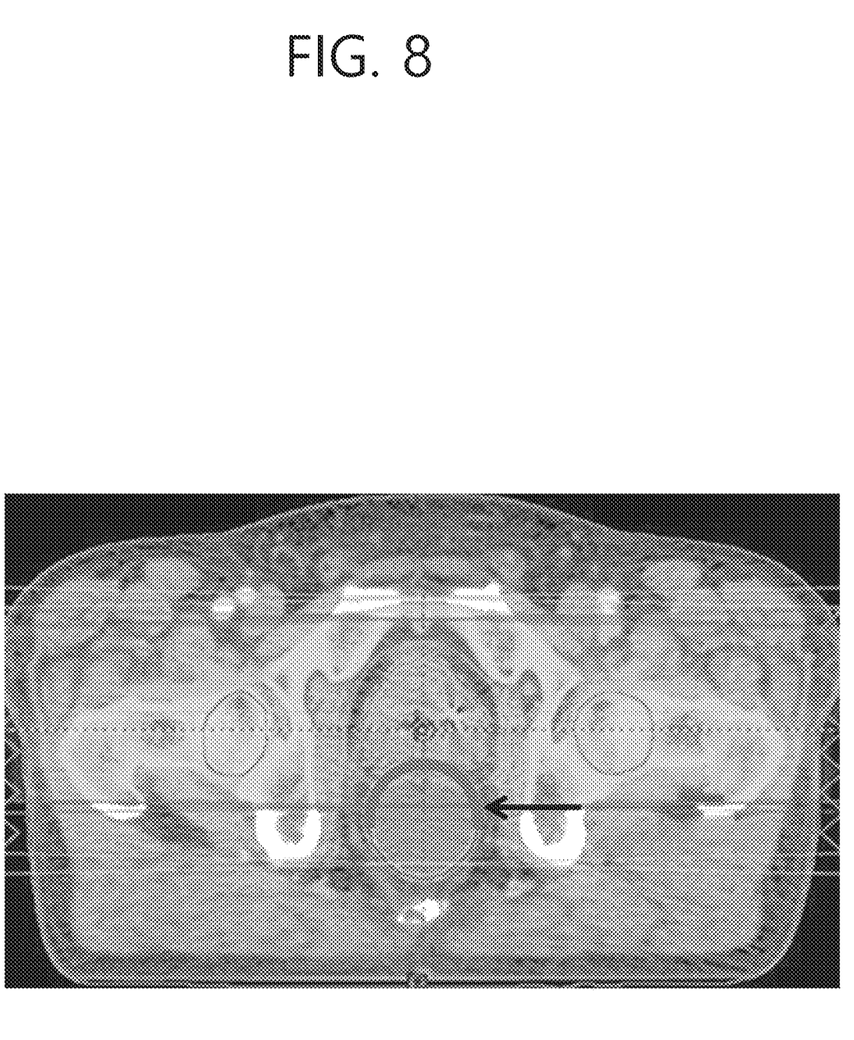
FIG. 8 is a computed tomography (CT) image showing a state in which the in vivo radiation dose measuring device according to the first embodiment of the present invention is actually inserted into the body.

Thereafter, when the in vivo radiation dose measuring device 1 is positioned at a desired site, the in vivo radiation dose measuring device 1 performs radiation treatment after the setup of a patient is completed. The expanded state suppresses the movement of the prostate and maintains the shape of the rectum constantly, thereby improving the accuracy of the treatment. FIG. 8 shows a state in which the in vivo radiation dose measuring device is inserted in the rectum through the anus in the radiation therapy of prostate cancer. The thick semicircular portion indicated by the arrow in the drawing is a radiation-sensitive film.

According to the present invention, the two-dimensional dose distribution of radiation delivered to the rectum of a patient by radiation therapy is measured by the radiation measurement part 30 in the form of a film. In the expanded state, the radiation measurement part 30 maintains a shape of a non-overlapping single layer, so that the dose distribution can be measured over a very wide area. In addition, the radiation measurement part 30 is in close contact with the surrounding tissue due to the expansion, so that the radiation dose in the surrounding tissue can be accurately measured.

According to the statistical analysis of clinical patients, the probability of occurrence of radiation side effects in normal organs is significantly increased if a limited dose of radiation or more radiation is delivered to a particular volume of each organ. Since the use of a conventional point dosimeter can actually obtain a dose value at only one point, the dose of radiation delivered to a particular volume is difficult to obtain. According to the present invention, the two-dimensional radiation dose distribution can be measured by the film-type radiation measurement part 30, and thus, so that such a conventional problem can be solved.

Also, according to the present invention, the accurate position of the in vivo radiation dose measuring device 1 can be understood through the position indication part 50, and even when the treatment is repeatedly performed several times to several tens of times, the radiation measurement part 30 can be always positioned at the same site. Therefore, an accurate total dose distribution can be obtained through the dose distribution data that have been obtained from the measurements in the treatment procedure each time After the end of the radiation treatment, the in vivo radiation measuring device 1 is made in a shrunken state by removing the fluid, and then the fluid is discharged out of the body.

Figure 9:
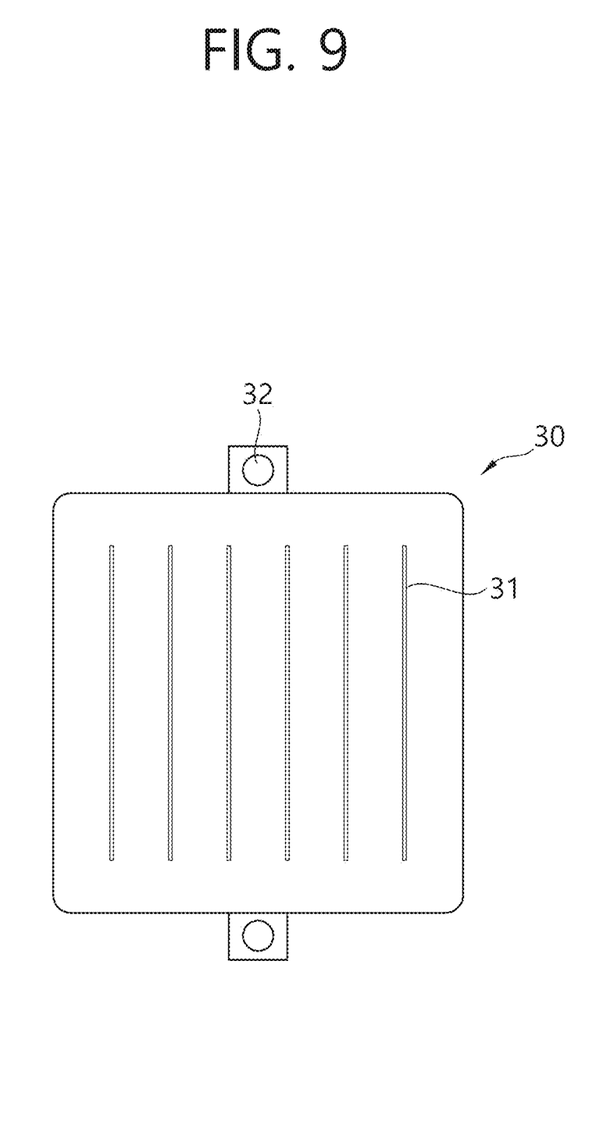
FIG. 9 is a plane view of a radiation measurement part of an in vivo radiation dose measuring device according to a second embodiment of the present invention.

Hereinafter, an in vivo radiation dose measuring device according to a second embodiment of the present invention will be described with reference to FIG. 9. FIG. 9 is a plane view of a radiation measurement part of the in vivo radiation dose measuring device according to the second embodiment of the present invention.

A radiation measurement part 30 according to the second embodiment has a film type as in the first embodiment, and has fold lines 31 formed by incisions.

Meanwhile, fixation counterparts 32 of the radiation measurement part 30 according to the second embodiment are formed to protrude outward.

The radiation measurement part 30 may be variously modified other than the type in the second embodiment. For example, the fold lines 31 may be formed by decreasing the thickness of the film instead of employing incisions, or by intermittent incisions. That is, the fold lines 31 may be formed by several methods as long as the radiation measurement part 30 can be easily folded. In addition, the radiation measurement part 30 may be prepared by connecting a plurality of band-shaped radiation films. Both ends of the fold line 31 may be treated in a linear or curved shape as in the first embodiment.

Meanwhile, the radiation measurement part 30 may be prepared without fold lines 31 as long as the radiation measurement part 30 is sufficiently thin so that a radiation detection layer inside is not damaged regardless of bending or winding. In this case, the radiation measurement part 30 wrap the expansion part 20 not in a polygonal shape, but in a shape corresponding to the expansion part 20 or in a circular or semicircular shape.

Hereinafter, an in vivo radiation dose measuring device according to a third embodiment of the present invention will be described with reference to FIGS. 10 and 11.

Figure 10:
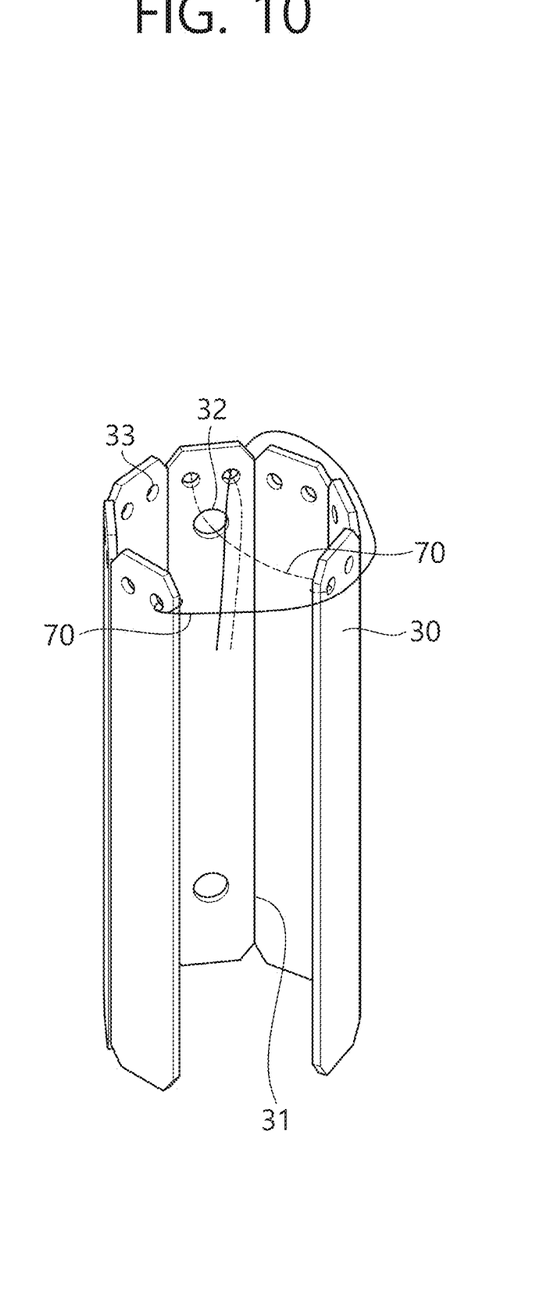
FIG. 10 shows a radiation measurement part and a shrinkage auxiliary part of an in vivo radiation dose measuring device according to a third embodiment of the present invention.
Figure 11:
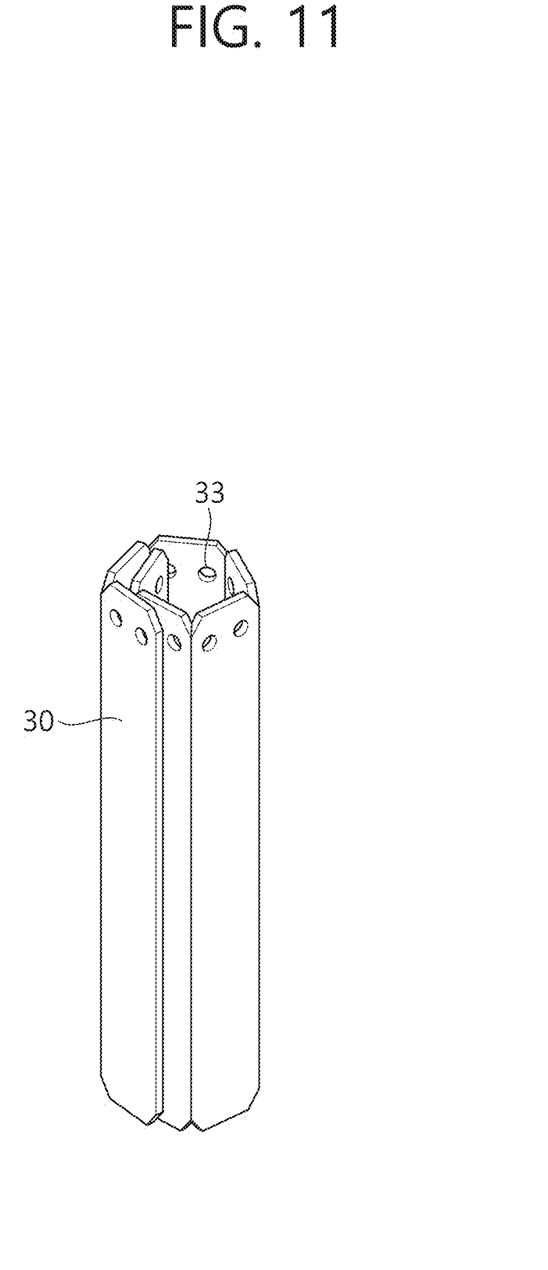
FIG. 11 shows an operation state of the shrinkage auxiliary part in the in vivo radiation dose measuring device according to the third embodiment of the present invention.

FIG. 10 shows a radiation measurement part 30 and a shrinkage auxiliary part 70 of an in vivo radiation dose measuring device according to a third embodiment of the present invention; and FIG. 11 shows an operation state of the shrinkage auxiliary part in the in vivo radiation dose measuring device according to the third embodiment of the present invention. The shrinkage auxiliary part is not shown in FIG. 11.

The in vivo radiation dose measuring device according to the third embodiment is configured to solve a problem in that the radiation measurement part 30, which have been unfolded in the body due to the expansion of the expansion part 20, is not properly folded upon the shrinkage of the expansion part 20.

A shrinkage auxiliary part 70 is prepared in a string type, and one end thereof is connected to an auxiliary hole 33 of the radiation measurement part 30. The auxiliary hole 33 connected to the shrinkage auxiliary part 70 is provided at a portion of the radiation measurement part 30, which is distant from the end portion of the main body 10 (in FIG. 5, the portion at which the gas discharge hole 15 is located), that is, at a portion of the radiation measurement part 30, which is in first contact with the anus when the in vivo radiation dose measuring device is drawn out from the body. The other end of the shrinkage auxiliary part 70 is exposed to the outside through the main body tube 11, and to this end, a separate passage hole may be formed in the main body tube 11.

In the embodiment, the shrinkage auxiliary part 70 is prepared by having two disconnected portions (indicated by a solid line and dotted line, respectively). In another embodiment, the shrinkage auxiliary part 70 may have a wire type, or may be prepared in a single type.

In cases where the radiation measurement part 30 is not properly folded, the end portion of the radiation measurement part 30 is compulsorily in close contact with the expansion part 20 by pulling the shrinkage auxiliary part 70 exposed to the outside. The medical staff can safely withdraw the in vivo radiation dose measuring device 1 out of the body while the end portion of the radiation measurement part 30 is in close contact with the expansion part to have a reduced diameter.

Hereinafter, an in vivo radiation dose measuring device according to a fourth embodiment of the present invention will be described with reference to FIGS. 12 and 13.

Figure 12:
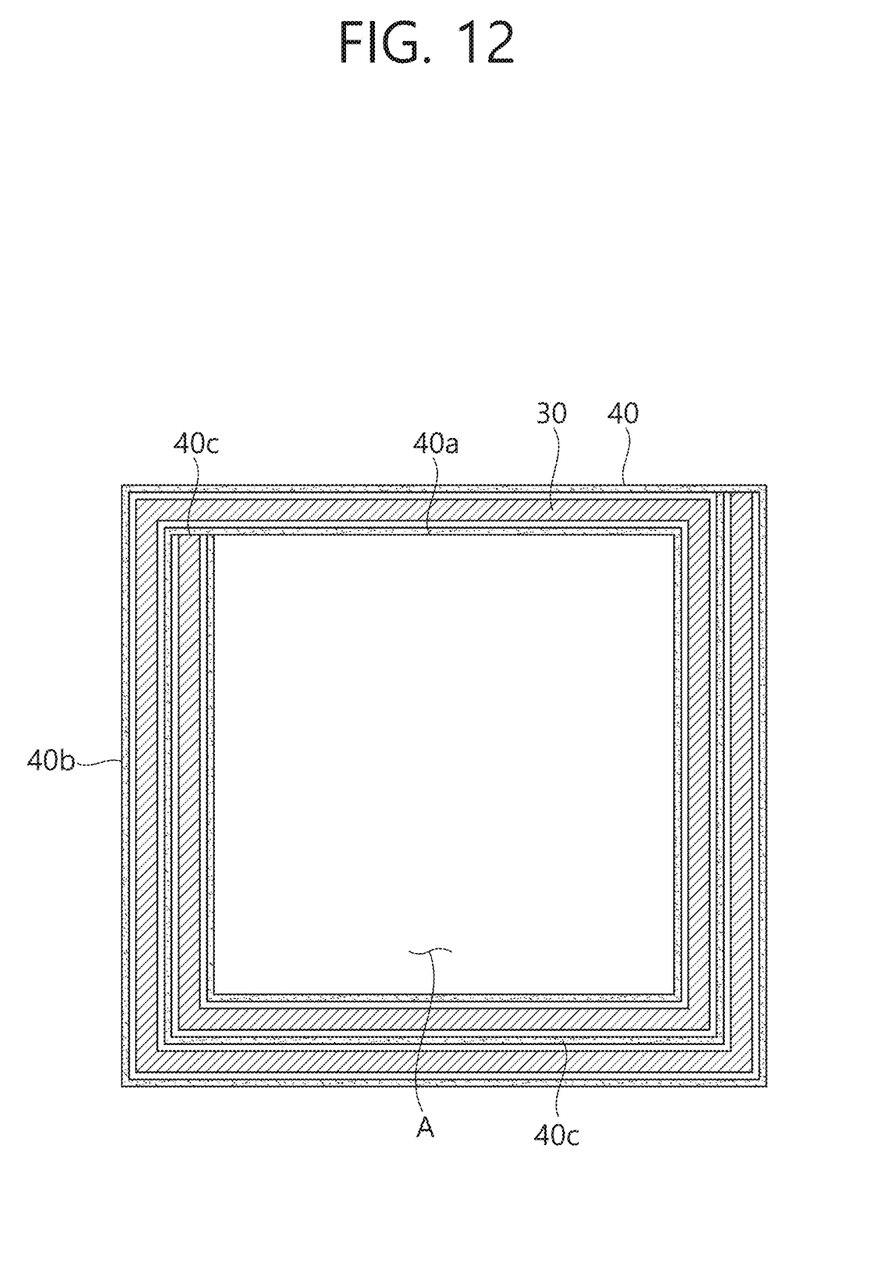
FIG. 12 shows a shrunken state of an in vivo radiation dose measuring device according to a fourth embodiment of the present invention.
Figure 13:
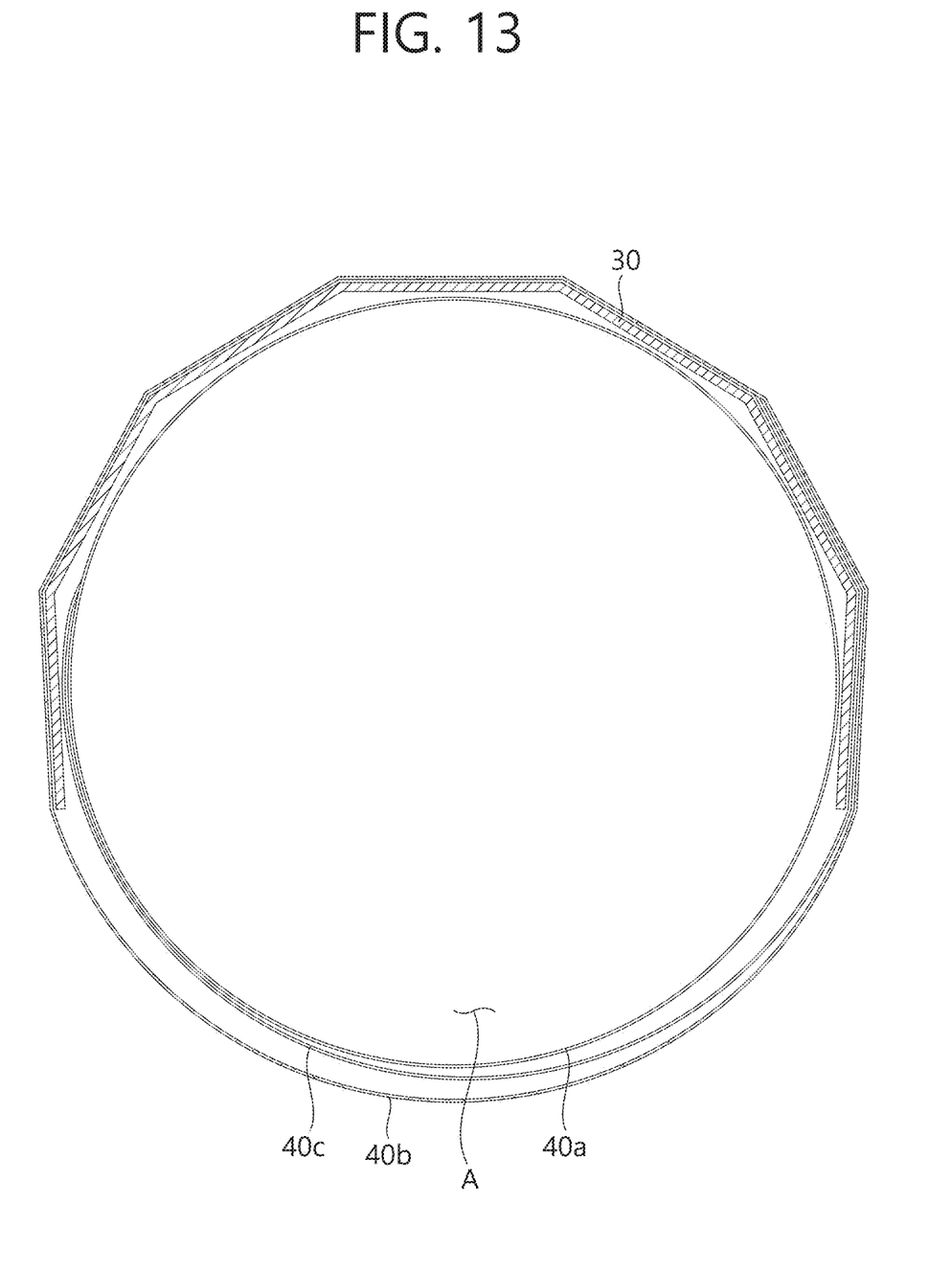
FIG. 13 shows an expanded state of the in vivo radiation dose measuring device according to the fourth embodiment of the present invention.

FIG. 12 shows a shrunken state of an in vivo radiation dose measuring device according to a fourth embodiment of the present invention; and FIG. 13 shows an expanded state of the in vivo radiation dose measuring device according to the fourth embodiment of the present invention.

FIGS. 12 and 13 show states corresponding to FIGS. 2 and 4, respectively. A main body tube 11 and an expansion part 20 are not shown. In FIGS. 12 and 13, a radiation measurement part 30 and an accommodation part 40 are shown apart from each other for convenience of explanation.

The accommodation part 40 according to the fourth embodiment is composed of a first portion 40a forming a closed curve inside, a second portion 40b forming a closed curve outside, and a third portion 40c connecting the first portion 40a and the second portion 40b.

The main body tube 11 and the expansion part 20 are positioned at the first portion 40a, and the radiation measurement part 30 is positioned at the second portion 40b.

In the fourth embodiment, the accommodation part 40 also performs a shrinking role while the shrinkage part 60 is omitted, unlike in the first embodiment. Referring to FIGS. 12 and 13, the accommodation part 40 of the radiation measurement part 30 is divided into two accommodation spaces by the third portion 40c. Such a division structure allows the radiation measurement part 30 to be smoothly folded at the time of shrinkage of the expansion part 20 such that the expansion part 20 and the radiation measurement part 30 interfere with each other, and can provide greater shrinking force compared with the first embodiment. Therefore, in the fourth embodiment, a separate shrinkage part 60 may be omitted.

The above-described embodiments are illustrative of the present invention, and the present invention is not limited thereto. Since numerous variations and modifications will become apparent to those skilled in the art once the above disclosure is fully appreciated, the scope and spirit of the invention come within the scope of the appended claims and their equivalents.

What is claimed is:

1. An in vivo radiation dose measuring device, comprising:
    a main body extending along a direction of in vivo insertion and being capable of supplying a fluid;
    an expansion part having at least a portion fixed or connected to the main body and being expandable and shrinkable by inflow and outflow of the fluid, the expansion part having a fixation element that protrudes outward;
    a film-type radiation measurement part that wraps around at least a portion of the expansion part, the radiation measurement part disposed on the expansion part to measure a 2-dimensional dose distribution of radiation in an in vivo tissue which the expansion part expands to touch; and
    an accommodation part that is transformable in compliance with a shape change of the radiation measurement part;
    wherein the radiation measurement part unfolds upon expansion of the expansion part and returns to a form wrapped around the expansion part upon shrinkage of the expansion part, and
    wherein the radiation measurement part has a fixation counterpart that corresponds to the fixation element, the fixation counterpart comprising a hole.

2. The in vivo radiation dose measuring device of claim 1, wherein the radiation measurement part has one or more fold lines parallel with the direction of insertion, the fold lines being formed in a direction in which the radiation measurement part wraps the expansion part.

3. The in vivo radiation dose measuring device of claim 1, wherein the accommodation part and the expansion part are in contact with each other, and
    wherein at least one of the accommodation part and the expansion part is formed of or treated with a material for reducing frictional force therebetween.

4. The in vivo radiation dose measuring device of claim 1, wherein the accommodation part forms a pocket and is in contact with the radiation measurement part.

5. The in vivo radiation dose measuring device of claim 4, wherein the accommodation part is formed of an elastic material.

6. The in vivo radiation dose measuring device of claim 5, wherein the accommodation part is formed of at least one of polyurethane, nylon, and polyester.

7. The in vivo radiation dose measuring device of claim 1, wherein the expansion part is formed of at least one of silicone, polyurethane, nylon, natural rubber, and synthetic rubber.

8. The in vivo radiation dose measuring device of claim 1, further comprising a position indication part for determining an insertion position of the radiation dose measuring device from outside a body upon the insertion of the radiation dose measuring device into the body.

9. The in vivo radiation dose measuring device of claim 1, further comprising a position indication part for determining an insertion position of the radiation dose measuring device from outside a body upon the insertion of the radiation dose measuring device into the body,
    wherein the position indication part is positioned on the fixation element.

10. The in vivo radiation dose measuring device of claim 1, further comprising a shrinkage part formed outside the accommodation part, wherein the shrinkage part gives shrinking force to the radiation measurement part upon the shrinkage of the expansion part.

11. The in vivo radiation dose measuring device of claim 10, wherein the shrinkage part is formed of an elastic material.

12. The in vivo radiation dose measuring device of claim 11, wherein the shrinkage part is formed of at least one of polyurethane, nylon, polyester, silicone, natural rubber, and synthetic rubber.

13. The in vivo radiation dose measuring device of claim 1, wherein the accommodation part comprises:
    a first portion wrapping the expansion part; and
    a second portion connected with the first portion to wrap the radiation measurement part,
    wherein the accommodation part gives shrinking force to the expansion part.

14. The in vivo radiation dose measuring device of claim 1, further comprising a shrinkage auxiliary part connected to a plurality of sites of the radiation measurement part, one end of the shrinkage auxiliary part protruding out of a body when the radiation dose measuring device is inserted into the body, wherein the shrinkage auxiliary part is capable of additionally shrinking the radiation measurement part by operating a portion of the shrinkage auxiliary part protruding out of the body.

15. The in vivo radiation dose measuring device of claim 14, wherein the shrinkage auxiliary part shrinks a portion of the radiation measurement part at an end of the radiation measurement part that is first inserted into the body.

\* \* \* \* \*